(12) United States Patent
Roemisch et al.

(10) Patent No.: US 7,863,009 B2
(45) Date of Patent: Jan. 4, 2011

(54) MUTANTS OF THE FACTOR VII-ACTIVATING PROTEASE AND DETECTION METHODS USING SPECIFIC ANTIBODIES

(75) Inventors: Juergen Roemisch, Marburg (DE); Hans-Arnold Stoehr, Wetter (DE); Annette Feussner, Marburg (DE); Wiegand Lang, Cölbe (DE); Thomas Weimer, Gladenbach (DE); Margret Becker, Marburg (DE); Claudia Nerlich, Marburg (DE); Gudrun Muth-Naumann, Wetter (DE); Bernd Knoblauch, Lich (DE)

(73) Assignee: CSL Behring GmbH, Marburg (DE)

( * ) Notice: Subject to any disclaimer, the term of this patent is extended or adjusted under 35 U.S.C. 154(b) by 169 days.

(21) Appl. No.: 12/232,350

(22) Filed: Sep. 16, 2008

(65) Prior Publication Data

US 2009/0162871 A1 Jun. 25, 2009

Related U.S. Application Data

(62) Division of application No. 10/930,754, filed on Sep. 1, 2004, now Pat. No. 7,442,514, which is a division of application No. 09/912,559, filed on Jul. 26, 2001, now Pat. No. 6,831,167.

(30) Foreign Application Priority Data

| Jul. 26, 2000 | (DE) | ................................. | 100 36 641 |
| Oct. 10, 2000 | (DE) | ................................. | 100 50 040 |
| Oct. 21, 2000 | (DE) | ................................. | 100 52 319 |
| Apr. 12, 2001 | (DE) | ................................. | 101 18 706 |

(51) Int. Cl.
  *G01N 33/53* (2006.01)
(52) U.S. Cl. ...................... 435/7.1; 435/7.92; 436/506
(58) Field of Classification Search ...................... None
  See application file for complete search history.

(56) References Cited

U.S. PATENT DOCUMENTS

| 5,175,087 | A | 12/1992 | Ranby et al. |
| 5,968,759 | A | 10/1999 | Roemisch et al. |
| 6,528,299 | B1 | 3/2003 | Roemisch et al. |
| 6,670,455 | B1 | 12/2003 | Roemisch et al. |
| 6,677,440 | B1 | 1/2004 | Roemisch et al. |
| 6,911,334 | B2 | 6/2005 | Roemisch et al. |
| 7,153,679 | B2 | 12/2006 | Kiechl et al. |
| 2002/0110552 | A1 | 8/2002 | Roemisch et al. |
| 2003/0077271 | A1 | 4/2003 | Roemisch et al. |
| 2003/0124622 | A1 | 7/2003 | Roemisch et al. |
| 2003/0215447 | A1 | 11/2003 | Roemisch et al. |
| 2004/0063187 | A1 | 4/2004 | Roemisch et al. |
| 2004/0186277 | A1 | 9/2004 | Roemisch et al. |
| 2005/0202002 | A1 | 9/2005 | Roemisch et al. |

FOREIGN PATENT DOCUMENTS

| CA | 2 311 479 A1 | 10/2000 |
| DE | 199 26 531.3 | 6/1999 |
| DE | 199 03 693 A1 | 10/1999 |
| DE | 100 23 923 | 12/2000 |
| DE | 199 37 218 A1 | 2/2001 |
| DE | 199 37 219 A1 | 2/2001 |
| DE | 100 36 641.4 | 2/2002 |
| EP | 0 952 215 A2 | 10/1999 |
| EP | 1 033 405 A2 | 9/2000 |
| EP | 1 059 359 A2 | 12/2000 |
| EP | 1 074 615 A1 | 2/2001 |
| EP | 1 074 616 A1 | 2/2001 |
| EP | 1 182 258 | 2/2002 |

OTHER PUBLICATIONS

Campbell, A., Monoclonal Antibody Technology, 1984, Elsevier Science Publishers B.V., pp. 1-32.*
Goding, James W. Monoclonal Antibodies:Principles and Practice, 1983, Academic Press, pp. 56-97.*
N. H.-Choi-Miura, et al. "Purification and Characterization of a Novel Hyaluronan-Binding Protein (PHBP) from Human Plasma: It Has Three EGF, a Kringle and a Serine Protease Domain, Similar to Hepatocyte Growth Factor Activator" *J. Biochem.*, 119(6):1157-65 (1996).
A. Hunfeld, et al. "Identification of the Thrombin-Like Activity of PCCs" *Annals of Hematology*, (76 Suppl. 1):A101 (1998).
A. Hunfeld, et al. "Detection of a Novel Plasma Serine Protease During Purification of Vitamin K-dependent Coagulation Factors" *FEBS Letters*, 456:290-94 (1999).

(Continued)

*Primary Examiner*—Michael Szperka
(74) *Attorney, Agent, or Firm*—Finnegan, Henderson, Farabow, Garrett & Dunner, L.L.P.

(57) ABSTRACT

Mutants of the DNA sequence coding for the protease (FSAP) which activates blood clotting factor VII and single-chain plasminogen activators, the mutants comprising a G/C base exchange at nucleotide position 1177 and/or a G/A base exchange at nucleotide position 1601, are described. The corresponding protease has a Glu/Gln exchange at amino acid position 393 and/or a Gly/Glu exchange at amino acid position 534. Diagnostic methods which are used for detecting FSAP in body fluids or tissue cells and also for identifying patients with genetic heterozygous or homozygous FSAP expression are also described. In addition, antibodies against FSAP and its mutants are disclosed and diagnostic methods which can be used to detect antibodies against FSAP and its mutants are specified.

8 Claims, No Drawings

OTHER PUBLICATIONS

J. Römisch, et al. "A Protease Isolated from Plasma which Activiates FVII in a Tissue Factor Independent Manner but Inactivates FV and FVIII" *Annals of Hematology*, (78 Suppl. 1):A10 (1999).

J. Römisch, et al. "The FVII Activating Protease Mediates Fibrinolytic Effects Activating Single-Chain Plasminogen Activators" *Annals of Hematology*, (78 Suppl. 1):A24 (1999).

J. Römisch, et al. "A Protease Isolated from Human Plasma Activating Factor VII Independent of Tissue Factor" *Blood Coagul. Fibrinol.*, 10:471-479 (1999).

J. Römisch, et al. "The FVII Activating Protease Cleaves Single-Chain Plasminogen Activators" *Haemostasis*, (29):292-299 (1999).

J. Römisch et al., "Quantitation of the Factor VII- and Single Chain Plasminogen Activator-Activating Protease in Plasmas of Healthy Subjects," *Blood Coagulation and Fibrinolysis*,12(5):375-383 (2001).

N.-H. Choi-Miura et al., "Proteolytic Activation and Inactivation of the Serine Protease Activity of Plasma Hyaluronan Binding Protein," *Biol. Pharm. Bull.*, 24(5):448-452 (2001).

J. Willeit et al., "Marburg I Polymorphism of Factor VII-Activating Protease: A Prominent Risk Predictor of Carotid Stenosis," *Circulation*, 107(5):667-670 (2003).

J. Römisch "Factor VII Activating Protease (FSAP): A Novel Protease in Hemostasis," *Biol. Chem.*, 383:1119-1124 (2002).

J. Römisch et al., "The Frequent *Marburg I* Polymorphism Impairs the Pro-Urokinase Activating Potency of the Factor VII Activating Protease (FSAP)," *Blood Coagulation and Fibrinolysis*,13(5):433-441 (2002).

Kitamura (Mar. 29, 1995) GenBank accession D49742.

K. Laake et al., "Activation of Purified Plasma Factor VII by Human Plasmin, Plasma Kallikrein, And Activated Components of the Human Intrinsic Blood Coagulation System," *Thrombosis Research*, vol. 5 (6): 759-772 (1974).

K. Hashimoto et al., "Cloning of the cDNA for a Mouse Homologue of Human PHBP: A Novel Hyaluronan-Binding Protein," *Biol. Pharm. Bulletin*, vol. 20(11): 1127-1130 (1997).

J-I. Sumiya et al., "Isolation and Characterization of the Plasma Hyaluronan-Binding Protein (PHBP) Gene (HABP2)," *J. Biochem.*, vol. 122: 983-990 (1997).

M. Etscheid et al., "Characterization of a Novel Serine Protease From Plasma," (1999) (Abstract).

A. Vostrov et al., "Plasma Hyaluronan-binding Protein Is a Serine Protease," *J. Biological Chemistry*, vol. 275 (30): 22978-22985 (2000).

T. Prins et al., "Cloning and characterization of a glutathione S-transferase homologue from the plant pathogenic fungus *Boyrytis cineria*," *Molecular Plant Pathology*, 1:169-178 (2000).

P.M. Colman, "Effects of amino acid sequence changes on antibody-antigen interactions," *Research in Immunology*, 145:33-36 (1994).

M. Etscheid et al., "Activation of proPHBSP, the zymogen of a plasma hyaluronan binding serine protease, by an intermolecular autocatalytic mechanism," *Biol. Chem.* 381:1223-1231 (2000).

Harlow et al., "Antibodies, A Laboratory Manual," Cold Spring Harbor Laboratories, pp. vi and 319-358 (1988).

C. Janeway et al., "Immunobiology," $3^{rd}$ ed., Garland Publishing, Inc., pp. 2:8-2:11 (1997).

Rose et al., "Manual of Clinical Immunology," $5^{th}$ ed., pp. 21-22 (1997).

F. Hofman, "Immunohistochemistry," in *Current Protocols in Immunology*, John Wiley & Sons, Inc., pp. 5.8.1-5.8.22 (1996).

Gallagher et al., "Immunoblotting and Immunodetection," in *Current Protocols in Immunology*, John Wiley & Sons, Inc., pp. 8.10.1-8.10.21 (1998).

* cited by examiner

SEQUENCE LISTING

<160> NUMBER OF SEQ ID NOS: 4

<210> SEQ ID NO 1
<211> LENGTH: 1683
<212> TYPE: DNA
<213> ORGANISM: Homo sapiens

<400> SEQUENCE: 1

| | | | | | |
|---|---|---|---|---|---|
| atgtttgcca | ggatgtctga | tctccatgtt | ctgctgttaa | tggctctggt | gggaaagaca | 60 |
| gcctgtgggt | tctccctgat | gtctttattg | gaaagcctgg | acccagactg | gaccccctgac | 120 |
| cagtatgatt | acagctacga | ggattataat | caggaagaga | acaccagtag | cacacttacc | 180 |
| catgctgaga | atcctgactg | gtactacact | gaggaccaag | ctgatccatg | ccagcccaac | 240 |
| ccctgtgaac | acggtgggga | ctgcctcgtc | catgggagca | ccttcacatg | cagctgcctg | 300 |
| gctcctttct | ctgggaataa | gtgtcagaaa | gtgcaaaata | cgtgcaagga | caacccatgt | 360 |
| ggccggggcc | aatgtctcat | tacccagagt | cctccctact | accgctgtgt | ctgtaaacac | 420 |
| ccttacacag | gtcccagctg | ctcccaagtg | gttcctgtat | gcaggccaaa | cccctgccag | 480 |
| aatgggcta | cctgctcccg | gcataagcgg | agatccaagt | tcacctgtgc | ctgtcccgac | 540 |
| cagttcaagg | ggaaattctg | tgaaataggt | tctgatgact | gctatgttgg | cgatggctac | 600 |
| tcttaccgag | ggaaaatgaa | taggacagtc | aaccagcatg | cgtgccttta | ctggaactcc | 660 |
| cacctcctct | tgcaggagaa | ttacaacatg | tttatggagg | atgctgaaac | ccatgggatt | 720 |
| ggggaacaca | atttctgcag | aaacccagat | gcggacgaaa | agccctggtg | ctttattaaa | 780 |
| gttaccaatg | acaaggtgaa | atgggaatac | tgtgatgtct | cagcctgctc | agcccaggac | 840 |
| gttgcctacc | agaggaaag | ccccactgag | ccatcaacca | agcttccggg | gtttgactcc | 900 |
| tgtggaaaga | ctgagatagc | agagaggaag | atcaagagaa | tctatggagg | ctttaagagc | 960 |
| acggcgggca | agcacccatg | gcaggcgtcc | ctccagtcct | cgctgcctct | gaccatctcc | 1020 |
| atgcccagg | gccacttctg | tggtggggcg | ctgatccacc | cctgctgggt | gctcactgct | 1080 |
| gcccactgca | ccgacataaa | aaccagacat | ctaaaggtgg | tgctagggga | ccaggacctg | 1140 |
| aagaaagaag | aatttcatga | gcagagcttt | agggtggaga | agatattcaa | gtacagccac | 1200 |
| tacaatgaaa | gagatgagat | tccccacaat | gatattgcat | tgctcaagtt | aaagccagtg | 1260 |
| gatggtcact | gtgctctaga | atccaaatac | gtgaagactg | tgtgcttgcc | tgatgggtcc | 1320 |
| tttcctctg | ggagtgagtg | ccacatctct | ggctggggtg | ttacagaaac | aggaaaaggg | 1380 |
| tcccgccagc | tcctggatgc | caaagtcaag | ctgattgcca | acactttgtg | caactcccgc | 1440 |
| caactctatg | accacatgat | tgatgacagt | atgatctgtg | caggaaatct | tcagaaacct | 1500 |
| gggcaagaca | cctgccaggg | tgactctgga | ggcccctga | cctgtgagaa | ggacggcacc | 1560 |
| tactacgtct | atgggatagt | gagctgggc | ctggagtgtg | gaagaggcc | aggggtctac | 1620 |
| acccaagtta | ccaaattcct | gaattggatc | aaagccacca | tcaaaagtga | aagtggcttc | 1680 |
| taa | | | | | | 1683 |

<210> SEQ ID NO 2
<211> LENGTH: 1683
<212> TYPE: DNA
<213> ORGANISM: Homo sapiens

<400> SEQUENCE: 2

| | | | | | |
|---|---|---|---|---|---|
| atgtttgcca | ggatgtctga | tctccatgtt | ctgctgttaa | tggctctggt | gggaaagaca | 60 |

-continued

```
gcctgtgggt tctccctgat gtctttattg gaaagcctgg acccagactg gaccccctgac    120 cagtatgatt acagctacga ggattataat caggaagaga acaccagtag cacacttacc    180
catgctgaga atcctgactg gtactacact gaggaccaag ctgatccatg ccagcccaac    240
ccctgtgaac acggtgggga ctgcctcgtc catgggagca ccttcacatg cagctgcctg    300
gctcctttct ctgggaataa gtgtcagaaa gtgcaaaata cgtgcaagga caacccatgt    360
ggccggggcc aatgtctcat tacccagagt cctccctact accgctgtgt ctgtaaacac    420
ccttacacag gtcccagctg ctcccaagtg gttcctgtat gcaggccaaa ccctgccag    480 aatgggcta cctgctcccg gcataagcgg agatccaagt tcacctgtgc ctgtcccgac    540
cagttcaagg ggaaattctg tgaaataggt tctgatgact gctatgttgg cgatggctac    600
tcttaccgag ggaaaatgaa taggacagtc aaccagcatg cgtgccttta ctggaactcc    660
cacctcctct gcaggagaaa ttacaacatg tttatggagg atgctgaaac ccatgggatt    720
ggggaacaca atttctgcag aaacccagat gcggacgaaa agccctggtg ctttattaaa    780
gttaccaatg acaaggtgaa atgggaatac tgtgatgtct cagcctgctc agcccaggac    840
gttgcctacc agaggaaag ccccactgag ccatcaacca agcttccggg gtttgactcc    900
tgtggaaaga ctgagatagc agagaggaag atcaagagaa tctatggagg ctttaagagc    960
acggcgggca agcacccatg gcaggcgtcc ctccagtcct cgctgcctct gaccatctcc   1020
atgccccagg gccacttctg tggtggggcg ctgatccacc cctgctgggt gctcactgct   1080
gcccactgca ccgacataaa aaccagacat ctaaggtgg tgctagggga ccaggacctg   1140
aagaaagaag aatttcatga gcagagcttt agggtgcaga agatattcaa gtacagccac   1200
tacaatgaaa gagatgagat tccccacaat gatattgcat tgctcaagtt aaagccagtg   1260
gatggtcact gtgctctaga atccaaatac gtgaagactg tgtgcttgcc tgatgggtcc   1320
tttccctctg ggagtgagtg ccacatctct ggctggggtg ttacagaaac aggaaaaggg   1380
tcccgccagc tcctggatgc caaagtcaag ctgattgcca acacttttgtg caactcccgc   1440 caactctatg accacatgat tgatgacagt atgatctgtg caggaaatct tcagaaacct   1500
gggcaagaca cctgccaggg tgactctgga ggcccctga cctgtgagaa ggacggcacc   1560
tactacgtct atgggatagt gagctggggc ctggagtgtg agaagaggcc aggggtctac   1620
acccaagtta ccaaattcct gaattggatc aaagccacca tcaaaagtga agtggcttc   1680 taa                                                                  1683
```

<210> SEQ ID NO 3
<211> LENGTH: 560
<212> TYPE: PRT
<213> ORGANISM: Homo sapiens

<400> SEQUENCE: 3

```
Met Phe Ala Arg Met Ser Asp Leu His Val Leu Leu Leu Met Ala Leu
1               5                   10                  15

Val Gly Lys Thr Ala Cys Gly Phe Ser Leu Met Ser Leu Leu Glu Ser
            20                  25                  30

Leu Asp Pro Asp Trp Thr Pro Asp Gln Tyr Asp Tyr Ser Tyr Glu Asp
        35                  40                  45

Tyr Asn Gln Glu Glu Asn Thr Ser Ser Thr Leu Thr His Ala Glu Asn
    50                  55                  60

Pro Asp Trp Tyr Tyr Thr Glu Asp Gln Ala Asp Pro Cys Gln Pro Asn
65                  70                  75                  80
```

-continued

Pro Cys Glu His Gly Gly Asp Cys Leu Val His Gly Ser Thr Phe Thr
            85                  90                  95

Cys Ser Cys Leu Ala Pro Phe Ser Gly Asn Lys Cys Gln Lys Val Gln
            100                 105                 110

Asn Thr Cys Lys Asp Asn Pro Cys Gly Arg Gly Gln Cys Leu Ile Thr
            115                 120                 125

Gln Ser Pro Pro Tyr Tyr Arg Cys Val Cys Lys His Pro Tyr Thr Gly
            130                 135                 140

Pro Ser Cys Ser Gln Val Val Pro Val Cys Arg Pro Asn Pro Cys Gln
145                 150                 155                 160

Asn Gly Ala Thr Cys Ser Arg His Lys Arg Arg Ser Lys Phe Thr Cys
                165                 170                 175

Ala Cys Pro Asp Gln Phe Lys Gly Lys Phe Cys Glu Ile Gly Ser Asp
            180                 185                 190

Asp Cys Tyr Val Gly Asp Gly Tyr Ser Tyr Arg Gly Lys Met Asn Arg
            195                 200                 205

Thr Val Asn Gln His Ala Cys Leu Tyr Trp Asn Ser His Leu Leu Leu
        210                 215                 220

Gln Glu Asn Tyr Asn Met Phe Met Glu Asp Ala Glu Thr His Gly Ile
225                 230                 235                 240

Gly Glu His Asn Phe Cys Arg Asn Pro Asp Ala Asp Glu Lys Pro Trp
                245                 250                 255

Cys Phe Ile Lys Val Thr Asn Asp Lys Val Lys Trp Glu Tyr Cys Asp
            260                 265                 270

Val Ser Ala Cys Ser Ala Gln Asp Val Ala Tyr Pro Glu Glu Ser Pro
        275                 280                 285

Thr Glu Pro Ser Thr Lys Leu Pro Gly Phe Asp Ser Cys Gly Lys Thr
290                 295                 300

Glu Ile Ala Glu Arg Lys Ile Lys Arg Ile Tyr Gly Gly Phe Lys Ser
305                 310                 315                 320

Thr Ala Gly Lys His Pro Trp Gln Ala Ser Leu Gln Ser Ser Leu Pro
                325                 330                 335

Leu Thr Ile Ser Met Pro Gln Gly His Phe Cys Gly Gly Ala Leu Ile
            340                 345                 350

His Pro Cys Trp Val Leu Thr Ala Ala His Cys Thr Asp Ile Lys Thr
        355                 360                 365

Arg His Leu Lys Val Val Leu Gly Asp Gln Asp Leu Lys Lys Glu Glu
    370                 375                 380

Phe His Glu Gln Ser Phe Arg Val Glu Lys Ile Phe Lys Tyr Ser His
385                 390                 395                 400

Tyr Asn Glu Arg Asp Glu Ile Pro His Asn Asp Ile Ala Leu Leu Lys
                405                 410                 415

Leu Lys Pro Val Asp Gly His Cys Ala Leu Glu Ser Lys Tyr Val Lys
            420                 425                 430

Thr Val Cys Leu Pro Asp Gly Ser Phe Pro Ser Gly Ser Glu Cys His
        435                 440                 445

Ile Ser Gly Trp Gly Val Thr Glu Thr Gly Lys Gly Ser Arg Gln Leu
    450                 455                 460

Leu Asp Ala Lys Val Lys Leu Ile Ala Asn Thr Leu Cys Asn Ser Arg
465                 470                 475                 480

Gln Leu Tyr Asp His Met Ile Asp Asp Ser Met Ile Cys Ala Gly Asn
                485                 490                 495

```
Leu Gln Lys Pro Gly Gln Asp Thr Cys Gln Gly Asp Ser Gly Gly Pro
            500                 505                 510

Leu Thr Cys Glu Lys Asp Gly Thr Tyr Tyr Val Tyr Gly Ile Val Ser
            515                 520                 525

Trp Gly Leu Glu Cys Gly Lys Arg Pro Gly Val Tyr Thr Gln Val Thr
            530                 535                 540

Lys Phe Leu Asn Trp Ile Lys Ala Thr Ile Lys Ser Glu Ser Gly Phe
545                 550                 555                 560

<210> SEQ ID NO 4
<211> LENGTH: 560
<212> TYPE: PRT
<213> ORGANISM: Homo sapiens

<400> SEQUENCE: 4

Met Phe Ala Arg Met Ser Asp Leu His Val Leu Leu Met Ala Leu
  1               5                  10                  15

Val Gly Lys Thr Ala Cys Gly Phe Ser Leu Met Ser Leu Leu Glu Ser
            20                  25                  30

Leu Asp Pro Asp Trp Thr Pro Asp Gln Tyr Asp Tyr Ser Tyr Glu Asp
            35                  40                  45

Tyr Asn Gln Glu Glu Asn Thr Ser Ser Thr Leu Thr His Ala Glu Asn
 50                  55                  60

Pro Asp Trp Tyr Tyr Thr Glu Asp Gln Ala Asp Pro Cys Gln Pro Asn
 65                  70                  75                  80

Pro Cys Glu His Gly Gly Asp Cys Leu Val His Gly Ser Thr Phe Thr
                 85                  90                  95

Cys Ser Cys Leu Ala Pro Phe Ser Gly Asn Lys Cys Gln Lys Val Gln
            100                 105                 110

Asn Thr Cys Lys Asp Asn Pro Cys Gly Arg Gly Gln Cys Leu Ile Thr
            115                 120                 125

Gln Ser Pro Pro Tyr Tyr Arg Cys Val Cys Lys His Pro Tyr Thr Gly
            130                 135                 140

Pro Ser Cys Ser Gln Val Val Pro Val Cys Arg Pro Asn Pro Cys Gln
145                 150                 155                 160

Asn Gly Ala Thr Cys Ser Arg His Lys Arg Arg Ser Lys Phe Thr Cys
                165                 170                 175

Ala Cys Pro Asp Gln Phe Lys Gly Lys Phe Cys Glu Ile Gly Ser Asp
            180                 185                 190

Asp Cys Tyr Val Gly Asp Gly Tyr Ser Tyr Arg Gly Lys Met Asn Arg
            195                 200                 205

Thr Val Asn Gln His Ala Cys Leu Tyr Trp Asn Ser His Leu Leu Leu
            210                 215                 220

Gln Glu Asn Tyr Asn Met Phe Met Glu Asp Ala Glu Thr His Gly Ile
225                 230                 235                 240

Gly Glu His Asn Phe Cys Arg Asn Pro Asp Ala Asp Glu Lys Pro Trp
                245                 250                 255

Cys Phe Ile Lys Val Thr Asn Asp Lys Val Lys Trp Glu Tyr Cys Asp
            260                 265                 270

Val Ser Ala Cys Ser Ala Gln Asp Val Ala Tyr Pro Glu Glu Ser Pro
            275                 280                 285

Thr Glu Pro Ser Thr Lys Leu Pro Gly Phe Asp Ser Cys Gly Lys Thr
            290                 295                 300

Glu Ile Ala Glu Arg Lys Ile Lys Arg Ile Tyr Gly Gly Phe Lys Ser
305                 310                 315                 320
```

-continued

```
Thr Ala Gly Lys His Pro Trp Gln Ala Ser Leu Gln Ser Ser Leu Pro
            325                 330                 335
Leu Thr Ile Ser Met Pro Gln Gly His Phe Cys Gly Gly Ala Leu Ile
            340                 345                 350
His Pro Cys Trp Val Leu Thr Ala Ala His Cys Thr Asp Ile Lys Thr
            355                 360                 365
Arg His Leu Lys Val Val Leu Gly Asp Gln Asp Leu Lys Lys Glu Glu
    370                 375                 380
Phe His Glu Gln Ser Phe Arg Val Gln Lys Ile Phe Lys Tyr Ser His
385                 390                 395                 400
Tyr Asn Glu Arg Asp Glu Ile Pro His Asn Asp Ile Ala Leu Leu Lys
            405                 410                 415
Leu Lys Pro Val Asp Gly His Cys Ala Leu Glu Ser Lys Tyr Val Lys
            420                 425                 430
Thr Val Cys Leu Pro Asp Gly Ser Phe Pro Ser Gly Ser Glu Cys His
            435                 440                 445
Ile Ser Gly Trp Gly Val Thr Glu Thr Gly Lys Gly Ser Arg Gln Leu
    450                 455                 460
Leu Asp Ala Lys Val Lys Leu Ile Ala Asn Thr Leu Cys Asn Ser Arg
465                 470                 475                 480
Gln Leu Tyr Asp His Met Ile Asp Asp Ser Met Ile Cys Ala Gly Asn
            485                 490                 495
Leu Gln Lys Pro Gly Gln Asp Thr Cys Gln Gly Asp Ser Gly Gly Pro
            500                 505                 510
Leu Thr Cys Glu Lys Asp Gly Thr Tyr Tyr Val Tyr Gly Ile Val Ser
            515                 520                 525
Trp Gly Leu Glu Cys Glu Lys Arg Pro Gly Val Tyr Thr Gln Val Thr
    530                 535                 540
Lys Phe Leu Asn Trp Ile Lys Ala Thr Ile Lys Ser Glu Ser Gly Phe
545                 550                 555                 560
```

MUTANTS OF THE FACTOR VII-ACTIVATING PROTEASE AND DETECTION METHODS USING SPECIFIC ANTIBODIES

This application is a division of application Ser. No. 10/930,754, filed Sep. 1, 2004, now U.S. Pat. No. 7,442,514, which is a division of Ser. No. 09/912,559, filed Jul. 26, 2001, now U.S. Pat. No. 6,831,167. This application also claims priority to German Application Nos. 100 36 641.4, filed Jul. 26, 2000, 100 50 040.4, filed Oct. 10, 2000, 100 52 319.6, filed Oct. 21, 2000, and 101 18 706.8, filed Apr. 12, 2001. All of the above applications are incorporated by reference herein.

The invention relates to mutants of the blood clotting factor VII-activating protease (FSAP), to methods for detecting FSAP and its mutants at the protein level and also RNA/DNA level or in a tissue sample and also to specific antibodies for said detection methods.

The German patent application 199 03 693.4 already discloses a protease which has been isolated from blood plasma and which can activate clotting factor VII. Owing to this first finding, said protease was denoted factor VII-activating protease (FSAP). Detailed studies showed that FSAP is also a potent activator of single-chain plasminogen activators such as prourokinase or single-chain tissue plasminogen activator (sct-PA). Owing to these properties, possible applications of FSAP have been described, for example its application as coagulation-promoting agent based on FVII activation-assisted acceleration of coagulation. FSAP may also be used, alone or in combination with plasminogen activators, for fibrinolysis, for example in the case of thrombotic complications.

As described in the German patent applications 199 03 693.4 and 19926 531.3, assays for detecting the protease have been developed which make it possible to quantify both the FSAP antigen content and its activity, for example in the plasma. In this connection, antigen determination is preferably carried out by means of an ELISA assay. As described in the German patent application 19926 531.3 FSAP activity can be determined by quantifying the activation of prourokinase to urokinase and reaction of the latter with a chromogenic substrate by subsequently measuring the difference in extinction. Surprisingly, it was found during said activity assay that the FSAP incubation conditions and thus made activation of prourokinase possible. More recent studies have shown that FSAP is converted into the active form by self activation and thus, for example, can activate prourokinase or FVII. This is further supported by the abovementioned incubation conditions, i.e. neutral to alkaline pH, calcium ions and heparin. Moreover, most recent results indicate that prourokinase/urokinase (or single-chain and double-chain tPA) themselves cause or assist activation of single-chain FSAP.

Using the two abovementioned assay systems, i.e. the ELISA and prourokinase activation assay, more than 180 plasmas of healthy blood donors were studied. It was found that 5 to 10% of all samples had a markedly decreased potential of FSAP-effected prourokinase activation compared with a plasma pool (of more than 100 healthy donors) or with the average of the whole test group.

In contrast, average FSAP antigen values were measured in the majority of said donors (with decreased activity). It is assumed therefore that in the blood samples studied one or more FSAP modifications which would lead to reduced or missing activities could be present. The reason for this could be polymorphisms in the population, i.e. one or more mutations in the FSAP structures, which are indicated in a modification of the FSAP amino acid sequence, as was already assumed in the German patent application 199 26 531.3. The activities which are usually 50 to 70% lower than the average value of all donors studied indicate a heterozygous mutation. The resulting phenotype could be a probably equal presence of both FSAPs, namely the wild type FSAP and the mutant variant, in the plasma. Assuming the mutated variant had (almost) completely lost the property to activate prourokinase, then on average about half the activity would be measured. In addition, however, pseudohomozygous manifestations of heterozygous mutations of other proteins have also been described, in which merely the mutated protein which itself, however, had only lost part of the appropriately detected biological property was detectable.

In order to exclude that the deficiency or reduction in unknown potential cofactors is responsible for the detected reduction in FSAP activity, FSAP samples of three donors whose donated samples had repeatedly shown significantly reduced activity were purified. The highly purified proteins likewise showed a markedly reduced activity compared with FSAP purified from the plasma pool. This reduces the possibility of a cofactor influence and increases that of a protein modification in the abovementioned sense. A surprising result was the apparently unreduced potential for activating factor VII. For this reason, mutants of this kind are particularly suitable for the abovementioned application as clotting-promoting agent, as described in the German Patent application 199 03 693.4, since their fibrinolytic potential is apparently limited. Said mutants may be prepared recombinantly or transgenically based on the findings described below of the nucleotide sequence modifications. However, they may, like the corresponding FSAP protein (single-chain or double-chain FSAP), also be isolated directly from natural sources such as blood plasma. The German Patent applications 199 03 693.4, 199 37 219.5 and 199 37 218.7 have already described methods which involve preparation of FSAP, preferably with the aid of immunoabsorption, as is illustrated in detail in the German Patent application 100 36 641.4. However, as far as it is known, the monoclonal antibodies used up until now do not discriminate between FSAP wild type and FSAP mutants. Accordingly, only monoclonal antibodies reacting specifically with the mutants can be used for preparing the mutants. It is possible to obtain the antibodies by immunization with the mutant. It is also possible to use peptides with protein regions corresponding to amino acids 389 to 397 ( . . . SFRVQKIFK . . . ) and/or 534 to 539 ( . . . EKRPGV . . . ) of SEQ ID NO:4 for immunization and for generation of corresponding antibodies according to known methods. In addition, said antibodies are also used to specifically detect said mutants, for example as reagents in detection methods such as ELISA Western Blots, in immunohistology or in fluorescence assisted cell sorting (=FACS).

The genomic FSAP sequence was identified in the gene bank under accession no. AC 006097 by comparison with the known cDNA sequence (Choi-Miura, Accession No. S 83182) and intron and exon sequences were derived in the process. A total of 12 primer pairs was designed in order to be able to amplify the coding sequences in specific PCR reactions together with a small part of the respective flanking intron sequences.

First, genomic DNA from the blood of 2 subjects with reduced activity and from four subjects with normal prourokinase activity was isolated, amplified using all primer pairs and then the DNA sequence was determined using the PCR primer. The result is shown in Table 1. A total of 4 nucleotide positions in the coding region were polymorphic, i.e. at these positions two bases were detected simultaneously. It can therefore be assumed that these cases are heterozygous, having one wild type and one mutant allele. Two of these (at positions 183 and 957) are third base exchanges which do not result in amino acid exchange. The other two which were found only in the DNA of the subjects with reduced prourokinase activity lead to amino acid exchanges as depicted in Table 1.

TABLE 1

DNA sequence at nucleotide positions*

| Subject No. | ProUK activity | 183 | 957 | 1177 | 1601 |
|---|---|---|---|---|---|
| S83182 |  | T | G | G | G |
| 9689 | normal | T/C | G | G | G |
| 9690 | normal | T/C | G | G | G |
| 9704 | normal | T | G/A | G | G |
| 9706 | normal | T | G/A | G | G |
| 9714 | reduced | T | G | G/C | G/A |
| 971 | reduced | T | G | G/C | G/A |

*where 1 is A of the start codon

Amino acid at position*

| Subject No. | ProUK activity | NT* 183 AA* 61 | NT: 957 AA: 319 | NT: 1177 AA: 393 | NT: 1601 AA: 534 |
|---|---|---|---|---|---|
| S83182 |  | His | Lys | Glu | Gly |
| 9689 | normal | His | Lys | Glu | Gly |
| 9690 | normal | His | Lys | Glu | Gly |
| 9704 | normal | His | Lys | Glu | Gly |
| 9706 | normal | His | Lys | Glu | Gly |
| 9714 | reduced | His | Lys | Glu/Gln | Gly/Glu |
| 9715 | reduced | His | Lys | Glu/Gln | Gly/Glu |

*NT—Nucleotide position; AA—amino acid position

In order to study the correlation of the two mutations with reduced prourokinase activity, the DNAs of further individuals was sequenced at these positions. The result is summarized in Table 2. All 6 subjects having reduced prourokinase activity were heterozygous at the nucleotide position 1601 (Gly-Glu exchange), and four were additionally heterozygous at position 1177 (Glu-Gln exchange). None of the 11 subjects in total having normal prourokinase activity or prourokinase activity in the lower normal range had the abovementioned heterozygosities. This result suggests that at least the exchange in amino acid position 534 is causally linked to reduced prourokinase activity. Whether an amino acid exchange at position 393 only can lead to a reduction in prourokinase activity, is still uncertain at the moment.

TABLE 2

DNA sequence at nucleotide position

| Subject No. | ProUK activity | 1177 | 1601 |
|---|---|---|---|
| 9714 | Low | C/G | A/G |
| 9715 | Low | C/G | A/G |
| 9802 | Low | C/G | A/G |
| 10032 | Low | G | A/G |
| 10039 | Low | C/G | A/G |
| 10047 | Low | G | A/G |
| 9698 | Lower normal range | G | G |
| 9702 | Lower normal range | G | G |
| 9711 | Lower normal range | G | G |
| 9712 | Lower normal range | G | G |
| 10038 | Lower normal range | G | G |

TABLE 2-continued

DNA sequence at nucleotide position

| Subject No. | ProUK activity | 1177 | 1601 |
|---|---|---|---|
| 9689 | Normal | G | G |
| 9690 | Normal | G | G |
| 9704 | Normal | G | G |
| 9706 | Normal | G | G |
| 9803 | Normal | G | G |
| 10043 | Normal | G | G |

The invention thus relates to a mutant of the DNA sequence coding for the protease (FSAP) which activates blood clotting factor VII and single-chain plasminogen activators, which mutant comprise a G/C base exchange at nucleotide position 1177 and/or a G/A base exchange at nucleotide position 1601.

The nucleotide sequence SEQ ID NO:1 of the attached sequence listing represents the wild type sequence. The DNA sequence of the mutant with the two exchanges at nucleotide positions 1177 and 1601 is described by SEQ ID NO:2. The corresponding wild type amino acid sequence can be found in SEQ ID NO:3. SEQ ID NO:4 shows the mutant amino acid sequence with the two amino acid exchanges (Glu-Gln 393 and Gly-Glu 534).

The detection of the DNA and amino acid sequences mentioned in the sequence listing has created the conditions for developing diagnostic methods for identifying patients having genetic heterozygous or homozygous FSAP expression. It is possible to detect the mutations either in the genomic DNA or in the mRNA derived therefrom. However, they can also be detected successfully at their protein level using monoclonal or polyclonal antibodies which are directed against the mutant having the modified amino acid sequence or against the wild type.

This makes it necessary to produce antibodies suitable for this purpose and thus to develop reliable diagnostic methods and assay systems.

The invention therefore also relates to monoclonal antibodies against blood clotting factor VII-activating protease and its mutants and also to their use for the detection and activity determination of FSAP and its mutants.

Assay systems which make it possible both to quantify the FSAP antigen content and to determine FSAP activity, such as Western Blots or an enzyme immunoassay (ELISA), are already known per se from the German Patent applications 199 03 693.4 and 199 26 531.3.

Said assay systems are based on binding and/or detection of FSAP by specific monoclonal antibodies. Although immunization of, for example, mice, frequently leads to identification of many positive clones with respect to the expression of a specific monoclonal antibody, often only a few of said clones are suitable for the abovementioned tasks. It was therefore the object to detect specific monoclonal antibodies against blood clotting factor VII-activating protease which can be effectively used both for its purification and for its qualitative and quantitative detection and for determination of its activity.

We have found that these requirements are met to a high degree by monoclonal antibodies against blood clotting factor VII-activating protease, which are produced by hybridoma cell line DSM ACC2453 and hybridoma cell line DSM ACC2454.

Until recently, FSAP was purified mainly in its activated form. Conventional preparation methods such as column-chromatographic techniques, favor the rapid activation and subsequent inactivation of the protease. According to the invention, it is now possible to purify blood clotting factor VII-activating protease and especially its proenzyme with high yields by coupling one of the abovementioned antibodies to a support, equilibrating said antibody with a liquid containing the protease or its proenzyme and then, after washing, obtaining the protease or its proenzyme by elution.

Moreover, the mentioned antibodies are also suitable for detecting blood clotting factor VII-activating protease or its proenzyme using an immunoassay in which a) a sample which should contain the protease or its proenzyme is incubated with a first antibody of the invention, fixed to a solid support, and then, after washing out, a second labelled antibody of the invention is added and, after washing out again, the signal produced by the second antibody or other monoclonal or polyclonal antibodies is measured; or b) the protease or its proenzyme contained in the sample to be tested is fixed to a support, for example by a polyclonal antibody against the protease or its proenzyme and is detected with a labelled inventive antibody alone or in a mixture with an unlabelled inventive antibody and subsequent detection of the monoclonal antibody or c) a sample to be tested for the protease or its proenzyme is added to an inventive antibody fixed to a support in the presence of a labelled protease or its proenzyme and the signal produced by the label is measured.

Another possibility for detecting blood clotting factor VII-activating protease or its proenzyme is to carry out the detection using the Western Blot method by an immunological reaction with a labelled inventive antibody alone or in a mixture with an unlabelled inventive antibody and subsequent detection of the monoclonal antibody, for example by labelled protein A or G or a labelled monoclonal or polyclonal antibody directed against the monoclonal antibody.

Finally it is also possible to determine the activity of blood clotting factor VII-activating protease or its proenzyme in protein solutions by incubating the protein solution containing the protease and/or its proenzyme to a solid support to which an anti-protease monoclonal inventive antibody has been coupled beforehand and, after washing out the solid support, incubating the protease and its proenzyme fixed to said solid support with reagents allowing determination of their activity. The activity of the protease or its proenzyme can then be measured by photometric determination of the extinction appearing due to the action on chromogenic substrates.

Other possibilities for determining the activity of the protease or its proenzyme are to measure its action of inactivating blood clotting factors VII/VIIa or V/Va or its action of shortening blood clotting times in global clotting assays or its action of activating plasminogen activators or its action of activating blood clotting factor VII.

Both the complete monoclonal antibodies and their fragments such as F(ab')$_2$ or Fab are suitable for application in the abovementioned methods. After labeling with a radioactive or fluorescent or enzymatically active substance, the antibodies or their fragments are employed as detecting aids in an immunoassay or in a Western Blot detection method. The unlabelled monoclonal antibodies or fragments may likewise be employed, but then detection or immobilization is carried out, for example, by a labeled antibody, directed against the mouse antibody, or its labelled fragment (sandwich method). The inventive monoclonal antibodies or their fragments may be employed alone or as mixtures. This is particularly recommended for Western Blots, since SDS gel electrophoreses are frequently carried out under reducing conditions of the samples. Since the two FSAP polypeptide chains are linked to one another merely via a disulfide bridge, the molecule disintegrates during reduction into two chains, namely the heavy and the light chain, the former being recognized by the monoclonal antibody of DSM ACC2454 and the latter by the monoclonal antibody of DSM ACC2453. Thus, for the detection of both chains the two inventive monoclonal antibodies or their fragments are required.

The monoclonal antibodies according to the invention were prepared and characterized as follows:

Immunization

Three female balb/c mice (approx. 6 weeks old) were immunized with FVIII activator. The first injection consisted of 0.2 ml of the antigen (10:g) mixed with 0.2 ml of complete Freund's adjuvant. In the three following boost injections (each 2 weeks apart) the antigen (20:g in 0.2 ml) was administered without adjuvant (all injections i.p.). The immunogen was diluted in PBS. After the last injection, the serum titer was determined by means of indirect ELISA by coating a microtiter plate with FVII activator. The mouse with the highest serum titer was selected for the fusion.

Fusion

About three weeks after the last application, the antigen was administered on three successive days (10:g in 0.1 ml i.v.). On the next day (day 4) the mouse was sacrificed after taking blood. The spleen was removed and the spleen cells were isolated. The spleen cells were then fused with the murine myeloma cell line SP2/0-Ag 14. The fusion reagent was polyethylene glycol 4000 (Merck). The fusion was carried out using a modification of the oriGInal K_hler/Milstein method. The cells were distributed on 24-well culture plates. The medium used was Dulbecco mod. Eagle's medium with 10% fetal calf serum and HAT for selection. After about two weeks, the cell clones grown were transferred to the wells of a 48 well plate and coded.

Hybridoma Screening

The culture supernatant was taken from 1728 grown clones and assayed by means of ELISA for the presence of mouse IgG. With the aid of immobilized FVII activator, mouse IgG-positive supernatants were tested for specificity (ELISA). Of the cell lines assayed, 108 cell lines were identified as specific for FVII activator and stored in the frozen state.

The two hybridoma cell lines denoted DSM ACC2453 and DSM ACC2454 were selected for further studies. The specificity of the antibodies produced by said cell lines was confirmed by BIACORE and binding kinetics was determined. The two monoclonal antibodies are of the IgG1 type.

With the aid of the described antibodies against FSAP wild type and against its mutants it is possible to carry out diagnostic methods for detecting the mutants by a) incubating a sample which could contain the mutant with a first antibody as claimed in claim 7, fixed to a solid support, then, after washing, adding a second, labelled antibody as claimed in claim 7 or a labelled antibody directed against the wild type and, after washing out again, measuring the signal produced by the second antibody, or b) incubating a sample which could contain the mutant with a first antibody fixed to a solid support and directed against the wild type, then, after washing, adding a second, labelled antibody as claimed in claim 7 and, after washing out again, measuring the signal produced by the second antibody, or c) fixing the sample to be tested for the presence of the mutant to a support and detecting said sample with a labelled antibody as claimed in claim 7 alone or in a mixture with an unlabelled antibody and subsequent detection of the labelled antibody, or d) adding a sample to be tested for the presence of the mutant to an antibody as claimed in claim 7, fixed to a support, in the presence of a labelled mutant and measuring the signal produced by the label.

Preference is given to a diagnostic method in which the FSAP activity is measured by incubating the protease-containing sample to a solid support to which an anti-protease antibody as claimed in claim 7 has been coupled beforehand and, after washing out the solid support, incubating the protease fixed to said support with reagents which allow determination of its activity.

In this connection, the protease activity can be measured by photometric determination of the extinction appearing following the action on chromogenic substrates.

It is also possible to determine the protease activity by measuring its action of inactivating blood clotting factors VIII/VIIIa or V/Va or its action of shortening blood clotting times in global clotting assays or its action of activating plasminogen activators or its action of activating blood clotting factor VII.

Finally, there are also methods available in which the action of activating plasminogen activators is measured, by activating the single-chain urokinase (scuPA, single chain urokinase plasminogen activator) or the single-chain-tPA (sctPA, single chain tissue plasminogen activator).

The mutations responsible for the reduction of prourokinase activity can be detected at the DNA and RNA level by using methods as they are also applied for detecting single nucleotide polymorphisms, for example the cDNA amplification of the RNA or amplification of the genomic DNA and their subsequent sequencing;

the detection of the mutation at the cDNA level or genomic DNA level or their amplification by hybridization with sequence-specific probes which may also carry labels for the detection, such as enzymes, alkaline phosphatase, HRP and their substrates, fluorescent dyes, also reporter-quencher pairs (such as, for example, scorpions, molecular beacons, TaqMan probes), radioisotopes, chromophores, chemiluminescence labels and electrochemiluminescence labels) or by methods such as selective 2'-amine acylation, electrochemical oxidation of nucleic acids by "minor groove binder" oligonucleotide conjugates or by HPLC.

On the basis of the test results which were obtained by the abovementioned antigen assays and activity assays it was possible to study three groups of healthy donors regarding potential mutations at the genomic level. For this purpose, blood was taken from the donors and the blood cells were separated from the plasma by centrifugation. The plasmas were then used to quantify the FSAP antigen and activity levels and were divided according to the latter into three groups, namely into "high/average", "average/reduced" and "significantly reduced". The blood cells obtained were then used to extract DNA/RNA and the results depicted on page 5 and in table 1 were determined therefrom.

Based on the present results, it is now possible to detect rapidly one or both of the mutants described, no matter whether their genotype is heterozygous or homozygous, at the level of the corresponding FSAP nucleotide sequence.

Whereas the abovementioned antigen and activity assays reflected quite well the genotype in a healthy donor, this can become difficult or impossible when the FSAP plasma levels are influenced. Thus, parameters such as hormonal fluctuations, lifestyle, etc., but particularly pathological conditions, more or less strongly influence antigen and/or activity levels. As described in the German Patent application 199 26 531.3, the measurable FSAP activity during a heart attack can increase markedly compared with the normal value with scarcely increased antigen content, and, as a result, donors which have a reduced FSAP activity when healthy, now appear to be "average".

For example, studies on whether patients with FSAP mutation run an increased risk of suffering thrombotic complications such as heart attacks are possible only with difficulty, owing to the abovementioned restrictions. On the other hand, for example, liver failures may lead to reduced plasma levels, and this likewise may lead to misinterpretations of the "true" genetic predisposition. In contrast, an FSAP mutation assay at the DNA/RNA level is independent of temporary events. The combination of all of the assays mentioned allows a complete picture of the donor/patient, i.e. the evaluation of a potential mutation and of the acute state regarding an influence on the antigen-activity ratio. This may result in prophylactic and therapeutic measures.

As described above, exclusively heterozygous blood donors whose blood plasma contains normal FSAP at about 50% and the FSAP mutant at about 50% have been found up until now. This results in an about 50% reduced activity level of plasmas in which both types of FSAP molecules are present. Plasma pools which have been obtained from the blood of 100 and more donors therefore also contain 5 to 10% of FSAP mutants, depending on the population. This results in a corresponding probability to receive in blood transfusions donor blood plasma which contains the FSAP mutant. If blood containing this mutant is administered to a recipient who cannot produce said mutant, then said mutant may be recognized as extraneous and appropriate antibodies can be generated. Subsequent administration of the FSAP mutant at a later stage may lead to immunological reactions in the recipient the side effects of which are familiar to the skilled worker.

Conversely, in a homozygous blood recipient who produces merely the FSAP mutant but not normal FSAP, the latter is recognized as "extraneous" and the appropriate antibodies against it are produced.

FSAP affects hemostasis and the cellular processes connected therewith. By involvement in blood clotting and/or fibrinolysis, it also affects the wound healing reaction. Moreover, FSAP, due to its property of having a high affinity to glycosaminoglycans, can bind to cells and other matrices and therefore is probably physiologically and pathophysiologically involved in cell migration and cellular-proteolytic processes.

Anti-FSAP antibodies thus may influence all FSAP-mediated activities. In the case of autoantibodies against FSAP appearing, it is, in addition to an impairment of the physiological functions, possible that immunocomplexes (FSAP+ antibody) contribute to side effects of known autoimmune diseases. This may lead, for example locally in the endothelium, to vasculitides. Neutralization of FSAP activity as profibrinolytic agent could also contribute to a thrombosis-promoting state.

There is, therefore, the need for a diagnostic method for detecting the above described antibodies.

The invention therefore also relates to a diagnostic method for detecting antibodies against factor VII-activating protease (=FSAP) and/or against an FSAP mutant formed by the exchange of one or more amino acids, which method comprises letting a sample which could contain antibodies react with the FSAP and/or FSAP mutant which are fixed to a solid support, incubating after washing, the antibody bound to the protease(s) with a labelled human anti-immunoglobulin or a labelled protein A and determining the signal emitted by the bound labelled substance.

The diagnostic method of the invention is expediently carried out using the ELISA technique in which FSAP and/or the FSAP mutant are bound to a matrix, for example to a microtiter plate. For optimal presentation of FSAP and/or FSAP mutant, the plate may be coated beforehand with monoclonal or polyclonal antibodies or their F(ab')$_2$ or Fab fragments and then loading said plate with FSAP and/or the FSAP mutant. Since FSAP and the mutant bind very well to dextran sulfate, heparin and similar substances, the prior coating with said agents for FSAP binding is also possible. After washing, the support or the microtiter plate is, where appropriate, in addition blocked and washed using the agents known for this purpose, such as detergent or albumin, and then incubated with the solution to be assayed. FSAP antibody-containing solutions may be blood serum, plasma and other body fluids such as synovial fluids, CSF, sputum, tears or seminal plasma or else cell lysates.

After incubating and washing the support, a suitable detection agent is then used. The assay substances necessary for detecting the various antibody classes such as IgG, IgM, IgA, IgE and the subclasses belonging thereto are commercially available as labelled reagents. The antibody titer may be detected and quantified by a photometric determination measuring the extinction which is caused by cleavage of a chromogenic substrate by an enzyme coupled to the anti-human antibody. However, it is also possible to measure fluorescence which is emitted by a fluorescent group linked to the antibody used for detection. Finally, it is also possible to carry out the detection using radiometric measurement, if the substance used for detection is labelled with a radioactive group.

The determination of antibodies against FSAP and/or in particular FSAP mutants makes it possible to identify the risk involved in a blood transfusion prior to carrying out said blood transfusion and to avoid dangerous complications by suitable measures.

The invention further relates to a diagnostic method for the immunohistochemical detection of the blood clotting factor VII-activating protease, its proenzyme or its mutants or fragments, which method comprises letting an anti-protease, labelled, monoclonal or polyclonal antibody or one of its fragments react with a tissue sample, and washing out the unbound antibody or its fragments and determining the signal emitted from the bound antibody or one of its fragments.

The method may also be carried out by letting an unlabelled monoclonal or polyclonal antibody, directed against the protease, its proenzyme or mutants or fragments thereof, or one of its fragments react with the tissue sample, washing out the unbound antibody or its fragments, then letting a labelled anti-antibody react with the tissue and, after washing out the unbound labelled anti-antibody, determining the signal emitted from the bound anti-antibody or its fragments.

It was also found that monoclonal or polyclonal antibodies directed against FSAP are very well suited to detecting FSAP in tissue sections of human origin, when said antibodies are labelled with chromophoric or luminescent groups. Anti-FSAP polyclonal antibodies obtained by immunization of rabbits, sheep, goats or other mammals are suitable for said detection as well as monoclonal antibodies. Particularly suitable for the histological specific detection of FSAP which may be present both in the active form and in the proenzyme form or as fragment are the monoclonal antibodies of hybridoma cell lines DSM ACC 2453 and DSM ACC 2454. Complexes of activated FSAP with inhibitors such as antiplasmin may also be detected in this way. Suitable for this purpose are all common histological detection methods such as light microscopy, fluorescence microscopy and electron microscopy.

Suitable for detecting FSAP in the abovementioned methods are both the complete polyclonal and monoclonal antibodies and their fragments such as F(ab')$_2$ or Fab, as long as they are labelled with a detectable group. The abovementioned antibodies or their fragments may be applied alone or as a mixture. This is particularly recommended in case one of the recognized epitopes is obscured. For example, a protein domain may not be accessible for an antibody due to cellular association, but is bound by another antibody having specificity for a different FSAP region. Antibodies which are directed against human FSAP, the wild type and/or against mutants thereof and which are described in more detail in the German Patent application 10052319.6 may also be employed for detection of FSAP in tissue sections of human origin.

The findings obtained so far on the immunohistochemical detection of FSAP can be summarized as follows:
  FSAP is detected in almost all of the human tissues studied up until now;
  endocronologically active cells such as Leydig cells or the endocronologically active cells of the islets of Langerhans of the pancreas can be very strongly stained intracytoplasmatically using antibodies carrying chromophoric groups;
  epithelia and endothelia display according to their location a more or less strong intracytoplasmatic immunoreaction with antibodies against FSAP;
  gangliocytes and dendrites of the cortex display high concentrations of FSAP, and this is detected by a strong immunohistological color reaction with chromophoric antibodies;
  plasma cells display an intensive intracytoplasmatic coloration with chromophoric antibodies;
  mesenchymal stroma cells display in complex tissues only a weak or no color reaction toward FSAP.

FSAP is thus a protein which can be regarded as a normal cell constituent. So far FSAP was found located both intracellularly and extracellularly, with the former compartment being markedly more stainable. The inventive detection of FSAP by the mentioned antibodies or their fragments makes it possible to identify the following pathological processes:
  endocrinologically active tumors and neura-endocrine tumors;
  angiogenic endothelia and endothelia of the capillary endothelium; and also
  angiogenically active tumors such as gliomas and glioblastomas, but also, for example, vascular tumors such as hemangioendothelioma or hemangiopericytoma and angiosarcoma;
  wound healing reactions, granulation tissue and collagenoses;
  arteriosclerotic, (micro)thrombosed and necrotic areas;
  neurodegenerative disorders such as Alzheimer's disease, Parkinson's disease or as spongiform encephalitides, for example caused by prion proteins;
  gammopathies and myelomas.

FSAP is detected by using preferably monoclonal antibodies of hybridoma cell lines DSM ACC 2453 or DSM ACC 2454.

The diagnostic method of the invention is illustrated in more detail by the following example:

The immunohistochemical reactivity of the FSAP-specific monoclonal antibodies of hybridoma cell lines DSM ACC 2453 and DSM ACC 2454 was studied by preparing from adult human tissue and malignant urological tumors 10:m thick paraffin sections and subsequently dewaxing said sections which were treated in citrate buffer in the microwave for 3 times 5 minutes. First, an unlabelled antibody of the abovementioned hybridoma cell lines was allowed to react with said sections for 30 minutes. After washing out the tissue section, a labelled anti-mouse detection antibody was allowed to react with the tissue likewise for 30 minutes and then the bound FSAP antibody was made visible by forming the APAAP complex (Alkaline Phosphatase/Anti-Alkaline Phosphatase complex) and by staining with chromogen and counterstaining with hemalum.

As a negative control, each tissue was separately incubated with the detection antibody—without prior incubation with the FSAP antibody—in order to make potential unspecific reactions of the detection visible. In addition an antibody against a-keratin was included as a positive control. The results of the immunohistochemical study of normal human tissue are summarized in Table 1:

| Antibodies against FSAP, clone DSMZ ACC2454 and DSMZ ACC 2453 Human normal tissue | | | | | |
|---|---|---|---|---|---|
| | DSMZ ACC2454 | DSMZ ACC2453 | | 2454 | 2453 |
| Esophagus | | | Appendix | | |
| Squamous epithelium | 2+ | 2+ | Epithelia | 1+ | 3+ |
| Secretory units | 0 | 0 | Musculature | 1+ | 1+ |
| Acinar ducts | 2+ | 2+ | Lymphatic follicle | 1+ | 2+ |
| Musculature | 1+ | 1+ | Plasma cells | 2+ | 3+ |
| Stroma | 1+ | 1+-2+ | Vascular endothelium | 1+ | 1+ |
| Vascular endothelium | 2+ | 2+ | Pancreas | | |
| Cardia (stomach) | | | Epithelia | 1+ | 2+ |
| Faveolar epithelium | 0 | 0 | Islets of Langerhans | 3+ | 1+ |
| Glandulae cardiacae | 1+ | 2+ | Duct epithelium | 2+ | 2+ |
| Mucous secretory units | 0 | 0 | Vascular endothelium | 1+ | 1+ |
| Oxyntic glands | 3+ | 3+ | Salivary gland | | |
| Musculature | 1+ | 1+ | Mucous and units | 0 | 0 |
| Vascular endothelium | 1+ | 1+ | Serous end units | 1+ | 1+-2+ |
| Corpus (stomach) | | | Acinar ducts | 1+ | 1+ |
| Foveolar epithelium | 0 | 0-1+ | Striate ducts | 1+ | 1+ |
| Corpus gland body | 2+ | 2+ | Vascular endothelium | 0-1+ | 0-1+ |
| Musculature | 0 | 1+ | Liver | | |
| Vascular endothelium | 1+ | 1+ | Hepatocytes | 2+ | 2+ |
| Duodenum | | | Bile ducts | 0 | 0 |
| Epithelia | 0-1+ | 1+ | Vascular | 1+ | (1+) |
| Brunner's glands | 0 | 0 | Gall bladder | | |
| Musculature | 0 | 0-1+ | Epithelia | 1+ | 1+ |
| Lymphatic follicle | 1+ | 2+ | Musculature | 2+ | 1+ |
| Ganglion cells | 2+ | 3+ | Vascular | 2+ | 1+ |
| Vascular endothelium | 1+ | 1+ | Cystic duct | | |
| Small intestine | | | Epithelium | 3+ | 3+ |
| Epithelia | 2+ | 3+ | Musculature | 2+ | 1+ |
| Musculature | 1+ | 1+ | Gaglion cells | 3+ | 3+ |
| Stroma | 1+ | 2+ | Vascular | 2+ | 2+ |
| Ganglion cells | 3+ | 3+ | Testis | | |
| Vascular endothelium | 1+ | 1+ | Leydig cells | 3+ | 1+ |
| Colon/Rectum | | | Sertoli cells | 1+-2+ | 1+ |
| Epithelia | 1+ | 1+ | Germ cells | 1+-2+ | 1+ |
| Lymphatic follicles | 1+ | 1+ | Vascular endothelium | 1+ | 1+ |
| Plasma cells | 1+ | 1+ | Rete testis | | |
| Vascular endothelium | 1+ | 0 | Epithelium | 2+ | 2+ |
| | 3454 | 2453 | | 2454 | 2453 |
| Epididymis | | | Placenta | | |
| Epididymis duct | 2+ | 2+ | Chorionic | 3+ | 2+ |
| Efferent ductulus | 2+ | 2+ | Amniotic epithelium | 2+ | 2+ |
| Stroma | 1+ | 1+ | Decidual cells | 2+-3+ | 2+ |
| Vascular endothelium | 1+ | 1+ | Stroma cells | 0 | +/− |
| Seminal gland | | | Vascular endothelium | 1+ | 1+ |
| Epithelium | 2+ | 3+ | Fetal membranes | | |

-continued

Antibodies against FSAP, clone DSMZ ACC2454 and DSMZ ACC 2453
Human normal tissue

| Tissue | 2454 | 2453 | Tissue | 2454 | 2453 |
|---|---|---|---|---|---|
| Musculature | 1+ | 1+ | Amniotic epithelium | 3+ | 2+ |
| Vascular endothelium | 2+ | 2+ | Decidual cells | 3+ | 1+ |
| Deferent duct | | | Fibroblasts | 3+ | 1+-2+ |
| Epithelium | 2+ | 3+ | Cervix uteri | | |
| Longitudinal muscle layer | 0 | +/− | Glandular epithelium | 0 | 0 |
| Annular muscle layer | 2+ | 3+ | Vascular endothelium | 1+ | 0-1 |
| Vascular endothelium | 2+ | 3+ | Stroma | 1+ | 0-1 |
| Prostate | | | Fallopian tube | | |
| Glandular epithelium | 2+ | 2+ | Epithelium | 2+ | 3+ |
| Musculature | 1+ | 1+ | Musculature | 0 | 1+ |
| Vascular endothelium | 1+-2+ | 1+-2+ | Vascular endothelium | 1+ | 2+ |
| Kidney | | | Breast | | |
| Tubules | 2+ | 1+ | Epithelia mammary gland lobules | 2+ | 2+ |
| Glomerules | 0 | 0 | Duct epithelium secretory ducts | 2+ | 2+ |
| Medullary epithelium | 1+ | 1+ | Fibroblasts | 0 | 1+ |
| Vascular endothelium | 0-1+ | 0-1+ | Plasma cells | 2+ | 2+ |
| Bladder | | | Vascular endothelium | 1+ | 0 |
| Urothelium | 2+ | 1+-2+ | Thyroid | | |
| Musculature | 2+ | 1+ | Follicular epithelium | 2+ | 1+-2+ |
| Plasma cells | 2+ | 2+ | Stroma | 1+ | 1+ |
| Fibroblasts | 1+-2+ | 1+-2+ | Vascular | 1+ | 0 |
| Peripheral nerve | | 0 | Thymus | | |
| Adrenal gland | | | Hassall's bodies | 2+-3+ | 2+ |
| Glomerular zone | 2+ | 1+ | Follicles | 1+ | 2+ |
| Fascicular zone | 1+-2+ | (1+) | Mantle zone | (1+) | (1+) |
| Reticular zone | 3+ | (1+) | Starry sky macrophages | 1+ | 1+ |
| Medulla | 0 | 0 | Spleen | + | + |
| Vascular endothelium | 1+ | (1+) | Tonsils | +/− | +/− |
| Endometrium | | | Lymph nodes | +/− | +/− |
| Glandular epithelium | 3+ | 2+ | Maxillary sinus | | |
| Stroma cells | 0 | 1+ | Respiratory epithelium | 2+ | 2+ |
| Myometrium | 1+ | 1+ | Plasma cells | 3+ | 3+ |
| Vascular endothelium | 1+ | 2+ | Vascular endothelium | 1+ | 1+ |
| | 2454 | 2453 | | 2454 | 2453 |
| Lung | | | Fatty tissue | 2+ | 2+ |
| Bronchial epithelium | 2+ | 1+ | Vascular endothelium | 2+ | 2+ |
| Alveolar epithelium | 1+-2+ | 1+ | Skin | | |
| Bronchial glands | 1+ | 1+ | Epidermis | 2+ | 1+-2+ |
| Cartilage | 3+ | 1+ | Dermis | 1+ | 0 |
| Musculature | 1+ | 1+ | Hypodermis | (1+) | 0 |
| Alveolar macrophages | 2+ | 2+ | Sweat glands | 1+ | 0 |
| Elastic fibers | 2+-3+ | 2+-3+ | Vascular endothelium | 1+ | 0 |
| Vascular endothelium | 1+ | 1+ | Endocardium | 0 | 0 |
| Skeletal muscles | 2+ | 1+ | Fibroblasts | 2+-3+ | 2+-3+ |

0 = negative
1+ = weakly positive
2+ = moderately strong positive
3+ = strongly positive Endocrine cells such as the islets of Langerhans of the pancreas, the Leydig cells of the testicular interstitium, the decidual cells of the placenta and the oxyntic gland body of the stomach cardia and also the highly cylindrical epithelium of the cystic duct display a strong reaction which in part shows fine granules. Strongly positive reactions were observed in plasma cells located in tissue structures and ganglionic cells and nerve cells of the cortex. The decidual cells, the amniotic epithelium and the fibroblasts of fetal membranes displayed very strong immunohistological stainability as did the epithelium lining the seminal glands and the enterocytes of the small intestine.

Studies of formalin-fixed, paraffin-embedded tumor material of urological tumors displayed a weak to moderately strong intracytoplasmatical reaction of different differentiated adenocarcinomas of the prostate. Tumor cells of seminomatous testicular tumors showed only a weak intracytoplasmatic reaction while non-seminomatous tumors (embryonic carcinomas and chorionic carcinomas) had a widely increased stainability of the tumor cells, indicating increased concentrations of FSAP.

The diagnostic method of the invention thus allows an immunohistochemical detection of pathological processes in a wide variety of organs.

What is claimed is:

1. A method for detecting autoantibodies against Factor VII Activating Protease (FSAP) and/or one or more FSAP mutants formed by the exchange of one or more amino acids in a body fluid sample from an individual, which comprises letting the body fluid sample react with FSAP and/or FSAP mutants which are fixed to a solid support, washing the solid support, and detecting antibodies bound to the support.

2. The method as claimed in claim 1, wherein the antibodies bound to the support are detected by incubating the support with a labeled substance selected from anti-human immunoglobulin or antigen binding fragments thereof, protein A, and protein G, and determining the signal emitted by the labeled substance bound to the support.

3. The method as claimed in claim 1, wherein the antibodies bound to the support are detected by incubating the support with anti-human immunoglobulin or antigen binding fragments thereof, protein A, or protein G, wherein the immunoglobulin, protein A, or protein G is coupled to an enzyme, adding a chromogenic or fluorogenic substrate, and determining the signal caused by cleavage of the substrate by the enzyme.

4. The method as claimed in claim 1, wherein the antibodies bound to the support are detected by fluorescence measurement.

5. The method as claimed in claim 1, wherein the antibodies bound to the support are detected by radiometric measurement.

6. The method as claimed in claim 1, wherein the body fluid sample is a blood or plasma sample.

7. The method as claimed in claim 1, wherein the autoantibodies are against wild-type FSAP.

8. The method as claimed in claim 1, wherein the autoantibodies are against one or more FSAP mutants.

* * * * *